United States Patent [19]

Breuer

[11] Patent Number: 4,772,693
[45] Date of Patent: Sep. 20, 1988

[54] 2-OXO-1-((SUBSTITUTED SULFONYL)AMINO)-CARBONYL)AZETIDINES

[75] Inventor: Hermann Breuer, Schoenhofen, Fed. Rep. of Germany

[73] Assignee: E. R. Squibb & Sons, Inc., Princeton, N.J.

[21] Appl. No.: 68,595

[22] Filed: Jul. 1, 1987

[51] Int. Cl.⁴ .................... A61K 31/44; C07D 401/14; C07D 417/14; C07D 401/06
[52] U.S. Cl. ................................. 540/363; 540/357; 540/360; 540/364; 546/278; 548/311; 548/312
[58] Field of Search ................ 540/363, 364, 360, 357

[56] References Cited

U.S. PATENT DOCUMENTS 4,587,047  5/1986  Breuer et al. ................. 540/363

FOREIGN PATENT DOCUMENTS 0062876 10/1982 European Pat. Off. .
2181130  4/1987 United Kingdom .

OTHER PUBLICATIONS

Abstract No. 646 from 19864 ICAAC Meeting, "Antimicrobial Activities of 1-Carbacephem Compounds and Their Structure-Activity Relationships", Mochida et al.

*Primary Examiner*—Mark L. Berch
*Attorney, Agent, or Firm*—Lawrence S. Levinson; Donald J. Barrack

[57] ABSTRACT

Antibacterial activity is exhibited by 2-azetidinones having a 3-acylamino substituted and having an activating group in the 1-position of the formula

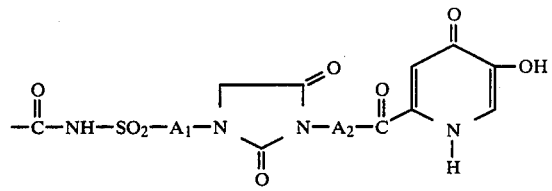

or

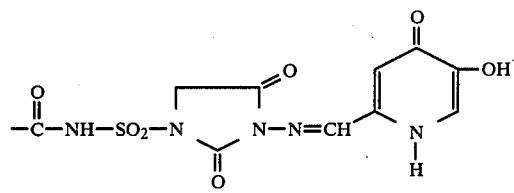

wherein $A_1$ is a single bond,

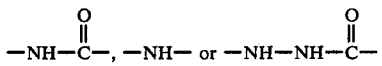

and $A_2$ is a single bond,

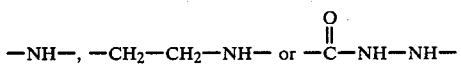

19 Claims, No Drawings

2-OXO-1-((SUBSTITUTED SULFONYL)AMINO)-CARBONYL)AZETIDINESZ

BRIEF DESCRIPTION OF THE INVENTION

Compounds having the formula

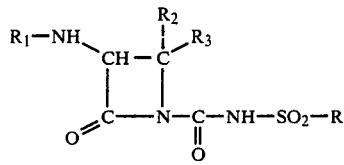
I and pharmaceutically acceptable salts thereof, exhibit antibacterial activity. In formula I, and throughout the specification, the symbols are as defined below.

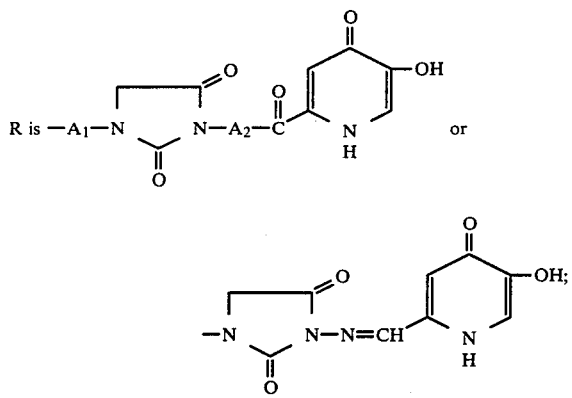

$R_1$ is an acyl group derived from a carboxylic acid;

$R_2$ and $R_3$ are the same or different and each is hydrogen, alkyl, alkenyl, alkynyl, cycloalkyl, phenyl, substituted phenyl or a 4, 5, 6 or 7-membered heterocycle (hereinafter referred to as $R_x$), or one of $R_2$ and $R_3$ is hydrogen and the other is azido, halomethyl, dihalomethyl, trihalomethyl, alkoxycarbonyl, 2-phenylethenyl, 2-phenylethynyl, carboxyl, —CH$_2$X$_1$ [wherein X$_1$ is azido, amino (—NH$_2$), hydroxy, carboxyl, alkoxycarbonyl, alkanoylamino, phenylcarbonylamino, (substituted phenyl)carbonylamino, alkylsulfonyloxy, phenylsulfonyloxy, (substituted phenyl)sulfonyloxy, phenyl, substituted phenyl, cyano,

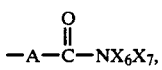

—S—X$_2$, or —O—X$_2$ (wherein A, X$_2$, X$_6$ and X$_7$ are as hereinafter defined)], —S—X$_2$ or —O—X$_2$ [wherein X$_2$ is alkyl, substituted alkyl, phenyl, substituted phenyl, phenylalkyl, (substituted phenyl)alkyl, alkanoyl, phenylalkanoyl, (substituted phenyl)alkanoyl, phenylcarbonyl, (substituted phenyl)carbonyl, or heteroarylcarbonyl],

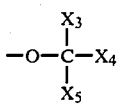

or

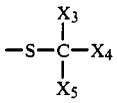

[wherein one of X$_3$ and X$_4$ is hydrogen and the other is hydrogen or alkyl, or X$_3$ and X$_4$ when taken together with the carbon atom to which they are attached form a cycloalkyl group; and X$_5$ is formyl, alkanoyl, phenylcarbonyl, (substituted phenyl)carbonyl, phenylalkylcarbonyl, (substituted phenyl)alkylcarbonyl, carboxyl, alkoxycarbonyl, aminocarbonyl

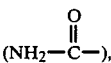

(substituted amino)carbonyl, or cyano (—C≡N)], or

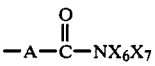

[wherein A is —CH≡CH—, —(CH$_2$)$_m$—, —(CH$_2$)$_m$—O—, —(CH$_2$)$_m$—NH—, or —CH$_2$—S—CH$_2$—, m is 0, 1 or 2, and X$_6$ and X$_7$ are the same or different and each is hydrogen, alkyl, phenyl or substituted phenyl, or X$_6$ is hydrogen and X$_7$ is amino, substituted amino, alkanoylamino or alkoxy, or X$_6$ and X$_7$ when taken together with the nitrogen atom to which they are attached form a 4, 5, 6 or 7-membered heterocycle];

A$_1$ is a single bond,

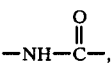

—NH— or

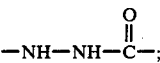

and

A$_2$ is a single bond, —NH—, —CH$_2$—CH$_2$—NH—, or

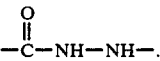

The above symbols (e.g., A$_1$, and A$_2$) are used to represent groups of multiple atoms. These groups are inserted in the structural formulas shown herein in the order in which they are presented (i.e., from left to right). For example, the group

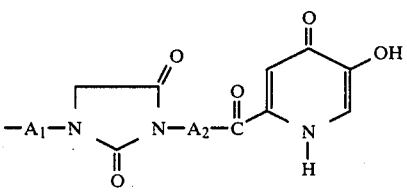

wherein A$_1$ is

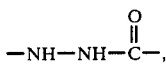

and $A_2$ is a single bond would be

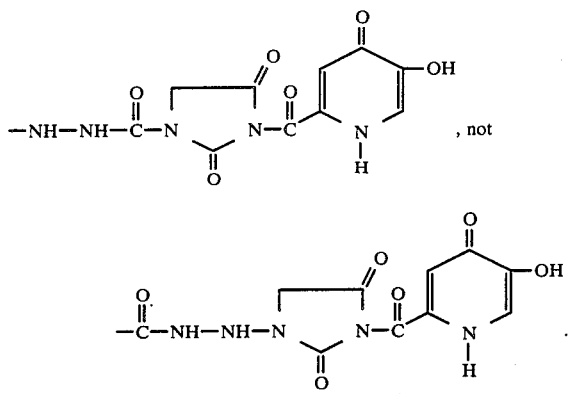

Listed below are definitions of various terms used to describe the β-lactams of this invention. These definitions apply to the terms as they are used throughout the specification (unless they are otherwise limited in specific instances) either individually or as part of a larger group.

The terms "alkyl" and "alkoxy" refer to both straight and branched chain groups. Those groups having 1 to 10 carbon atoms are preferred. The terms "cycloalkyl" and "cycloalkenyl" refer to cycloalkyl and cycloalkenyl groups having 3, 4, 5, 6 or 7 carbon atoms.

The term "substituted alkyl" refers to alkyl groups substituted with one or more (preferably 1, 2 or 3) azido, amino (—NH₂), halogen, hydroxy, carboxy, cyano, alkoxycarbonyl, aminocarbonyl, alkanoyloxy, alkoxy, phenyloxy, (substituted phenyl)oxy, mercapto, alkylthio, phenylthio, (substituted phenyl)thio, alkylsulfinyl, or alkylsulfonyl groups.

The terms "alkanoyl", "alkenyl", and "alkynyl" refer to both straight and branched chain groups. Those groups having 2 to 10 carbon atoms are preferred.

The terms "halogen" and "halo" refer to fluorine, chlorine, bromine and iodine.

The term "substituted phenyl" refers to a phenyl group substituted with 1, 2 or 3 amino (—NH₂), halogen, hydroxyl, trifluoromethyl, alkyl (of 1 to 4 carbon atoms), alkoxy (of 1 to 4 carbon atoms), alkanoyloxy, aminocarbonyl, or carboxy groups.

The expression "a 4, 5, 6 or 7-membered heterocycle" (referred to as "$R_x$") refers to substituted and unsubstituted, aromatic and non-aromatic groups containing one or more (preferably 1, 2 or 3) nitrogen, oxygen or sulfur atoms. Exemplary substituents are oxo (=O), halogen, hydroxy, nitro, amino, cyano, trifluoromethyl, alkyl of 1 to 4 carbons, alkoxy of 1 to 4 carbons, alkylsulfonyl, phenyl, substituted phenyl, 2-furfurylideneamino ( 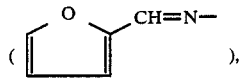 ), benzylideneamino and substituted alkyl groups (wherein the alkyl group has 1 to 4 carbons). One type of "4, 5, 6 or 7-membered heterocycle" is the "heteroaryl" group. The term "heteroaryl" refers to those 4, 5, 6 or 7-membered heterocycles which are aromatic. Exemplary heteroaryl groups are substituted and unsubstituted pyridinyl, duranyl, pyrrolyl, thienyl, 1,2,3,-triazolyl, 1,2,4-triazolyl, imidazolyl, thiazolyl, thiadiazolyl, pyrimidinyl, oxazolyl, triazinyl, and tetrazolyl. Exemplary nonaromatic heterocycles (i.e., fully or partially saturated heterocyclic groups) are substituted and unsubstituted azetidinyl, oxetanyl, thietanyl, piperidinyl, piperazinyl, imidazolidinyl, oxazolidinyl, pyrrolidinyl, tetrahydropyrimidinyl, dihydrothiazolyl and hexahydroazepinyl. Exemplary of the substituted 4, 5, 6 or 7-membered heterocycles are 1-alkyl-3-acetidinyl, 2-oxo-1-imidazolidinyl, 3-alkylsulfonyl-2-oxo-1-imidazolidinyl, 3-benzylideneamino-2-oxo-1-imidazolidinyl, 3-alkyl-2-oxo-1-imidazolidinyl, 3-phenyl (or substituted phenyl)-2-oxo-1-imidazolidinyl, 3-benzyl-2-oxo-1-imidazolidinyl, 3-(2-aminoethyl)-2-oxo-1-imidazolidinyl, 3-amino-2-oxo-1-imidazolidinyl, 3-[(alkoxycarbonyl)amino]-2-oxo-1-imidazolidinyl, 3-[2-[(alkoxycarbonyl)amino]ethyl]-2-oxo-1-imidazolidinyl, 2-oxo-1-pyrrolidinyl, 2-oxo-3-oxazolidinyl, 4-hydroxy-6-methyl-2-pyrimidinyl, 2-oxo-1-hexahydroazepinyl, 2-oxo-3-pyrrolidinyl, 2-oxo-3-tetrahydrofuranyl, 2,3-dioxo-1-piperazinyl, 2,5-dioxo-1-piperazinyl, 4-alkyl-2,3-dioxo-1-piperazinyl, and 4-phenyl-2,3-dioxo-1-piperazinyl.

The term "substituted amino" refers to a group having the formula —NX₈X₉ wherein X₈ is hydrogen, alkyl, phenyl, substituted phenyl, phenylalkyl or (substituted phenyl)alkyl, and X₉ is alkyl, phenyl, substituted phenyl, phenylalkyl, (substituted phenyl)alkyl, hydroxy, cyano, alkoxy, phenylalkoxy, or amino(—NH₂).

The term "acyl" refers to all organic radicals derived from an organic acid (i.e., a carboxylic acid) by removal of the hydroxyl group. Certain acyl groups are, of course, preferred but this preference should not be viewed as a limitation of the scope of this invention. Exemplary acyl groups are those acyl groups which have been used in the past to acylate β-lactam antibiotics including 6-aminopenicillanic acid and derivatives and 7-aminocephalosporanic acid and derivatives; see, for example, Cephalosporins and Penicillins, edited by Flynn, Academic Press (1972), German Offenlegungsschrift No. 2,716,677, published Oct. 10, 1978, Belgian Pat. No. 867,994, published Dec. 11, 1978, U.S. Pat. No. 4,152,432, issued May 1, 1979, U.S. Pat. No. 3,971,778, issued July 27, 1976, U.S. Pat. No. 4,172,199, issued Oct. 23, 1979, and British Pat. No. 1,348,894, published Mar. 27, 1974. The portions of these references describing various acyl groups are incorporated herein by reference. The following list of acyl groups is presented to further exemplify the term "acyl"; it should not be regarded as limiting that term. Exemplary acyl groups are:

(a) Aliphatic groups having the formula

wherein $R_a$ is alkyl; cycloalkyl; alkoxy; alkenyl; cycloalkenyl; cyclohexadienyl; or alkyl or alkenyl substituted with one or more halogen, cyano, nitro, amino, mercapto, alkylthio, or cyanomethylthio groups.

(b) Carbocyclic aromatic groups having the formula

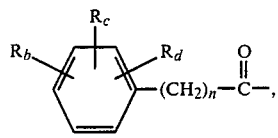

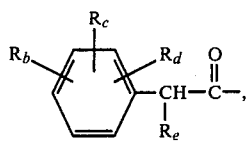

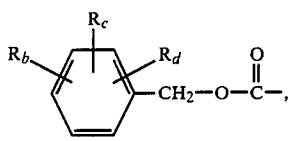

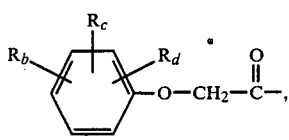

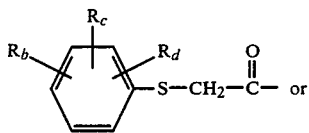

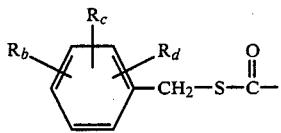

wherein n is 0, 1, 2 or 3; $R_b$, $R_c$, and $R_d$ each is independently hydrogen, halogen, hydroxyl, nitro, amino, cyano, trifluoromethyl, alkyl of 1 to 4 carbon atoms, alkoxy of 1 to 4 carbon atoms or aminomethyl; and $R_e$ is amino, hydroxyl, a carboxyl salt, protected carboxyl, formyloxy, a sulfo salt, a sulfoamino salt, azido, halogen, hydrazino, alkylhydrazino, phenylhydrazino, or [(alkylthio)thioxomethyl]thio.

Preferred carbocyclic aromatic acyl groups include those having the formula

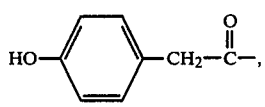

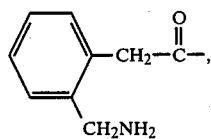

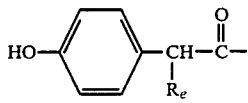

($R_e$ is preferably a carboxyl salt or sulfo salt) and

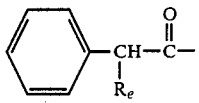

($R_e$ is preferably a carboxyl salt or sulfo salt).

(c) Heteroaromatic groups having the formula

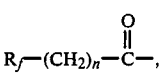

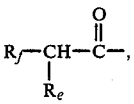

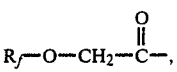

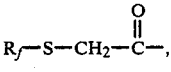

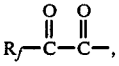

wherein n is 0, 1, 2 or 3; $R_e$ is as defined above; and $R_f$ is a substituted or unsubstituted 5-, 6- or 7-membered heterocylic ring containing 1, 2, 3 or 4 (preferably 1 or 2) nitrogen, oxygen and sulfur atoms. Exemplary heterocyclic rings are thienyl, furyl, pyrrolyl, pyridinyl, pyrazolyl, pyrazinyl, thiazolyl, pyrimidinyl, thiadiazolyl and tetrazolyl. Exemplary substituents are halogen, hydroxyl, nitro, amino, protected amino, cyano, trifluoromethyl, alkyl of 1 to 4 carbon atoms, alkoxy of 1 to 4 carbon atoms, or

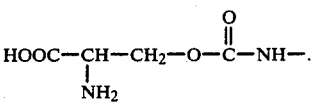

Preferred heteroaromatic acyl groups include those groups of the above formula wherein $R_f$ is 2-amino-4-thiazolyl, 2-amino-5-halo-4-thiazolyl, 4-aminopyrimidin-2-yl, 5-amino-1,2,4-thiadiazol-3-yl, 2-thienyl, 2-furanyl, or 6-aminopyridin-2-yl.

(d) [[(4-Substituted-2,3-dioxo-1-piperazinyl)carbonyl]amino]arylacetyl groups having the formula

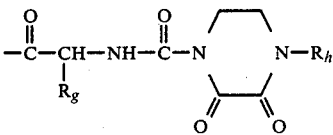

wherein $R_g$ is an aromatic group (including carbocyclic aromatics such as those of the formula

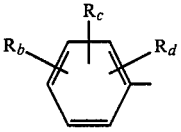

and heteroaromatics as included within the definition of $R_f$); and $R_h$ is alkyl, substituted alkyl (wherein the alkyl group is substituted with one or more halogen, cyano, nitro, amino or mercapto groups), arylmethyleneamino (i.e., —N=CH—$R_g$ wherein $R_g$ is as defined above), arylcarbonylamino (i.e., $$-NH-\overset{O}{\underset{\|}{C}}-R_g$$

wherein $R_g$ is as defined above) or alkylcarbonylamino.

Preferred [[(4-substituted-2,3-dioxo-1-piperazinyl)-carbonyl]amino]arylacetyl groups include those wherein $R_h$ is ethyl, phenylmethyleneamino or 2-furylmethyleneamino.

(e) (Substituted oximino)arylacetyl groups having the formula $$-\overset{O}{\underset{\|}{C}}-\underset{\underset{R_g}{|}}{C}=N-O-R_i$$

wherein $R_g$ is as defined above and $R_i$ is hydrogen, alkyl, cycloalkyl, $$\underset{-C-COOH}{\overset{CH_2-(CH_2)_{1,2\ or\ 3}}{\diagdown\diagup}},$$

2-pyrrazolylmethyl, (2-oxo-3-pyrrolidinyl)methyl, alkylaminocarbonyl, arylaminocarbonyl (i.e., $$-\overset{O}{\underset{\|}{C}}-NH-R_g$$

wherein $R_g$ is as defined above) or substituted alkyl (wherein the alkyl group is substituted with one or more halogen, cyano, nitro, amino, mercapto, alkylthio, aromatic group (as defined by $R_g$), carboxyl (including salts thereof), amido, alkoxycarbonyl, phenylmethoxycarbonyl, diphenylmethoxycarbonyl, hydroxyalkoxyphosphinyl, dihydroxyphosphinyl, hydroxy(phenylmethoxy)phosphinyl, dialkoxyphosphinyl or tetrazolyl substituents).

Preferred (substituted oxyimino)arylacetyl groups include those wherein $R_g$ is 2-amino-4-thiazolyl. Also preferred are those groups wherein $R_i$ is methyl, ethyl, carboxymethyl, 1-carboxy-1-ethyl, 1-carboxy-1-methylethyl, 2,2,2-trifluoroethyl, or 1-carboxycyclopropyl.

(f) (Acylamino)arylacetyl groups having the formula $$-\overset{O}{\underset{\|}{C}}-\underset{\underset{R_g}{|}}{CH}-NH-\overset{O}{\underset{\|}{C}}-R_j$$

wherein $R_g$ is as defined above and $R_j$ is

[structure with $R_b$, $R_c$, $R_d$ on ring, $-(CH_2)_n-O-$]

amino, alkylamino, (cyanoalkyl)amino, amido, alkylamido, (cyanoalkyl)amido, $$-CH_2-NH-\overset{NH}{\underset{\|}{C}}\diagup\text{(pyridyl)},\ -\underset{\underset{NH_2}{|}}{CH}-CH_2-\overset{O}{\underset{\|}{C}}-NH-CH_3,$$

[phenyl-pyridinone-SO$_2$—N(CH$_2$—CH$_2$—OH)$_2$ structure]

[HO-pyridine-CH$_3$ structure], [OH-naphthyridine structure],

[OH-pyrido-pyrimidine-piperazinyl-N—CH=O structure], or

[HO,HO-chromone-C(=O)- structure]

Preferred (acylamino)arylacetyl groups of the above formula include those groups wherein $R_j$ is amino or amido. Also preferred are those groups wherein $R_g$ is phenyl or 2-thienyl.

(g) [[[3-Substituted-2-oxo-1-imidazolidinyl]carbonyl]amino]arylacetyl groups having the formula $$-\overset{O}{\underset{\|}{C}}-\underset{\underset{R_g}{|}}{CH}-NH-\overset{O}{\underset{\|}{C}}-N\underset{\underset{CH_2-CH_2}{|}}{\diagdown}\overset{\overset{O}{\underset{\|}{C}}}{\diagup}N-R_k$$

wherein $R_g$ is as defined above and $R_k$ is hydrogen, alkylsulfonyl, arylmethyleneamino (i.e., —N=CH—$R_g$ wherein $R_g$ is as defined above), $$-\overset{O}{\underset{\|}{C}}-R_m$$

(wherein $R_m$ is hydrogen, alkyl or halogen substituted alkyl), aromatic group (as defined by $R_g$ above), alkyl or substituted alkyl (wherein the alkyl group is substituted with one or more halogen, cyano, nitro, amino or mercapto groups).

Preferred [[3-substituted-2-oxo-1-imidazolidinyl]carbonyl]amino]arylacetyl groups of the above formula include those wherein $R_g$ is phenyl or 2-thienyl. Also preferred are those groups wherein $R_k$ is hydrogen, methylsulfonyl, phenylmethyleneamino or 2-furylmethyleneamino.

The compounds of this invention form basic salts with various inorganic and organic bases which are also within the scope of this invention. Such salts include ammonium salts, alkali metal salts, alkaline earth metal salts, salts with organic bases, e.g., dicyclohexylamine, benzathine, N-methyl-D-glucamine, hydrabamine and the like. The pharmaceutically acceptable salts are preferred, although other salts are also useful, e.g., in isolating or purifying the product.

Some of the compounds of this invention may be crystallized or recrystallized from solvents containing water. In these cases, water of hydration may be formed. This invention contemplates stoichiometric hydrates as well as compounds containing variable amounts of water that may be produced by processes such as lyophilization.

The β-lactams of formula I contain at least one chiral center—the carbon atom in the 3-position of the β-lactam nucleus to which the acylamino substituent ("$R_1$—NH—") is attached. This invention is directed to those β-lactams which have been described above, wherein the stereochemistry at the chiral center in the 3-position of the β-lactam nucleus is the same as the configuration at the carbon atom in the 6-position of naturally occurring penicillins (e.g., penicillin G) and as the configuration at the carbon atom in the 7-position of naturally occurring cephamycins (e.g., cephamycin C). Also included within the scope of this invention are racemic mixtures which contain the above-described β-lactams.

DETAILED DESCRIPTION OF THE INVENTION

The β-lactams of formula I, and pharmaceutically acceptable salts thereof, have activity against gram-positive and gram-negative organisms. The compounds of this invention can be used as agents to combat bacterial infections (including urinary tract infections and respiratory infections) in mammalian species, such as domesticated animals (e.g., dogs, cats, cows, horses, and the like) and humans.

For combating bacterial infections in mammals, a compound of this invention can be administered to a mammal in need thereof in an amount of about 1.4 mg/kg/day to about 350 mg/kg/day, preferably about 14 mg/kg/day to about 100 mg/kg/day. All modes of administration which have been used in the past to deliver penicillins and cephalosporins to the site of the infection are also contemplated for use with β-lactams of this invention. Such methods of administration include oral, intravenous, intramuscular, and as a suppository.

The β-lactams of formula I can be prepared from a 3-protected amino-2-azetidinone having the formula

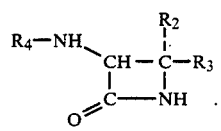
II

In formula II, and throughout the specification, the symbol "$R_4$" refers to an amino protecting group. These groups are well known in the field of β-lactam chemistry, and the particular group chosen is not critical. Benzyloxycarbonyl, trityl, and t-butoxycarbonyl are exemplary protecting groups. The reaction of a β-lactam of formula II with an isocyanate having the formula $$O=C=N-SO_2-Y,$$ III wherein Y is a leaving group such as chlorine, yields the corresponding compound having the formula

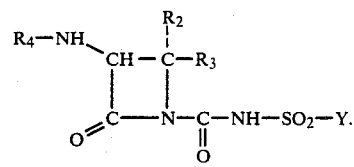
IV

The reaction is preferably run in an inert organic solvent, e.g., ethyl acetate, tetrahydrofuran, dimethoxyethane, dichloromethane, acetonitrile or mixtures of these solvents. Displacement of the leaving group "Y" with the desired group "R" can be accomplished using the appropriate nucleophile having the formula $$RH,$$ V optionally in the presence of a base (e.g., triethylamine), and yields the corresponding compound having the formula

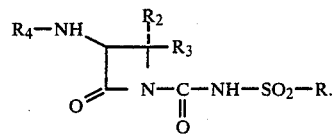
VI

Alternatively, the displacement of the leaving group can be accomplished by reaction of a compound of formula IV with a protected form of a compound of formula V. Following the displacement reaction, the protecting groups can be removed using art-recognized techniques to yield a compound of formula VI.

Protected forms of a compound of formula V, and of all reactants described herein which contain a 3-hydroxy-4-pyridone moiety, include those compounds wherein the hydroxyl group is protected, those compounds wherein the hydroxyl group and the ring nitrogen are protected, and those compounds wherein both pyridone oxygens are protected. Exemplary protecting groups are silyl (e.g., trimethylsilyl), benzyl and acyl (e.g., acetyl). If silyl is used, later deprotection can be accomplished using hydrolysis or fluoride mediated cleavage. If benzyl is used, later deprotection can be accomplished by hydrogenolysis. If acyl is used, later deprotection can be accomplished by hydrolysis.

Deprotection of a compound of formula VI using conventional techniques yields the corresponding key intermediate having the formula

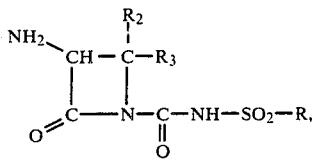

VII or a salt thereof. The particular deprotection reaction used will, of course, depend on the protecting group ("$R_4$") present. If, for example, $R_4$ is a t-butoxycarbonyl protecting group, deprotection can be accomplished by treatment of a compound of formula VI with acid (e.g., formic acid or trifluoroacetic acid). If, for example, $R_4$ is a benzyloxycarbonyl protecting group, deprotection can be accomplished by catalytic hydrogenation of a compound of formula VI. Alternatively, the $R_4$ protecting group can be removed simultaneously with the other pyridone protecting groups immediately following the above-described displacement reaction.

Well known acylation techniques can be used to convert an intermediate of formula VII to a corresponding product of formula I. Exemplary techniques include reaction of a compound of formula VII with a carboxylic acid ($R_1$—OH), or corresponding carboxylic acid halide or carboxylic acid anhydride. The reaction with a carboxylic acid proceeds most readily in the presence of a carbodiimide such as dicyclohexylcarbodiimide and a substance capable of forming an active ester in situ such as N-hydroxybenzotriazole. In those instances where the acyl group ($R_1$) contains reactive functionality (such as amino or carboxyl groups) it may be necessary to first protect those functional groups, then carry out the acylation reaction, and finally deprotect the resulting product.

An alternative procedure for preparing the compounds of formula I comprises first acylating (acylation techniques have been described above) a 3-amino-2-azetidinone having the formula

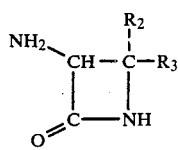

VIII to yield an intermediate having the formula

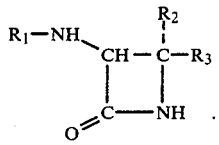

IX

A

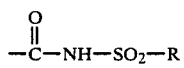

activating group can be introduced in the 1-position of a compound of formula IX (using the procedures described above) to obtain the corresponding product of formula I. In those instances wherein the acyl side-chain "$R_1$" contains reactive functionality (such as amino groups), it may be necessary to first protect those functional groups, then carry out the addition of the activating group in the 1-position, and finally deprotect the resulting product.

Still another synthesis for the preparation of compounds of formula I comprises the use of a 3-azido-2-azetidinone having the formula

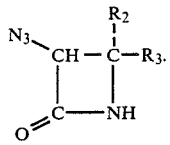

X

A

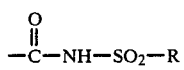

activating group can be introduced in the 1-position of a compound of formula X (using the procedures described above) to obtain the corresponding compound having the formula

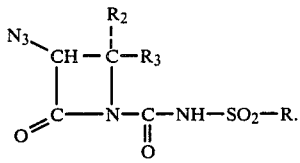

XI

Reduction of an intermediate of formula XI yields the corresponding intermediate having the formula

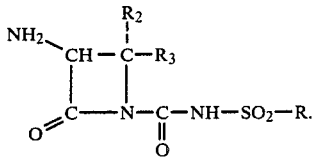

VII

The reduction can be accomplished by catalytic (e.g., palladium on charcoal or platinum oxide) hydrogenation or with reducing agents such as zinc or triphenylphosphine. As described above, from these key intermediates (compounds of formula VII), using conventional acylation techniques, it is possible to prepare the products of formula I.

Alternatively, a 3-azido-2-azetidinone of formula X can be reduced to the corresponding 3-amino-2-azetidinone having the formula

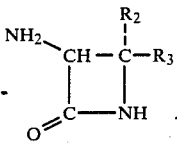

VIII

The reduction can be accomplished by catalytic (e.g., palladium on charcoal or platinum oxide) hydrogenation or with reducing agents such as zinc or triphenylphosphine. A 3-amino-2-azetidinone of formula VIII can be reacted as described above (i.e., first acylated and then treated as described above to introduce a

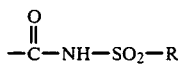

activating group in the 1-position) to yield the products of formula I.

Still another synthesis for preparing the compounds of formula I wherein $R_2$ and $R_3$ are each hydrogen utilizes a 6-acylaminopenicillanic acid having the formula

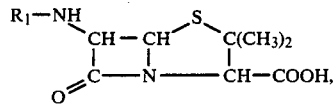

XII or a salt thereof, as the starting material. By adapting procedures described in the literature, 3-acylamino-2-azetidinone can be obtained from the corresponding 6-acylaminopenicillanic acid of formula XII: see, for example, *Chem. Soc. Special Publication* No. 28, pg. 288 (1977), *The Chemistry of Penicillins*, Princeton University Press, pg. 257, and *Synthesis*, 494 (1977).

As described in the literature 6-acylaminopenicillanic acid, or a salt thereof, can be desulfurized to yield a compound having the formula

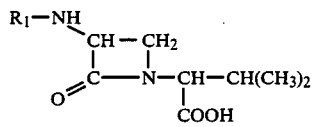

XIII by reduction using Raney nickel. The reaction can be run in water under reflux conditions.

Replacement of the carboxyl group of a compound of formula XIII with an acetate group followed by hydrolysis yields the corresponding 3-acylamino-2-azetidinone having the formula

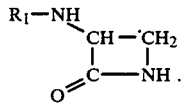

XIV

Treatment of a compound of formula XIII with cupric acetate and lead tetraacetate in an organic solvent (e.g., acetonitrile) replaces the carboxyl group with an acetate group. Hydrolysis of the resulting compound can be accomplished using potassium carbonate in the presence of sodium borohydride.

A

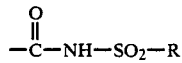

activating group can be introduced in the 1-position of a compound of formula XIV (yielding products of formula I wherein $R_2$ and $R_3$ are each hydrogen) using the procedures described above.

Still another variation of the above-described synthetic routes for preparing a compound of formula I wherein $R_2$ and $R_3$ are each hydrogen comprises first desulfurizing 6-aminopenicillanic acid, acylating the resulting compound to yield a compound of formula XIII and then proceeding as described above to obtain first a 3-acylamino-2-azetidinone of formula XIV and then a product of formula I.

The azetidinones of formula I can also be prepared from amino acids having the formula

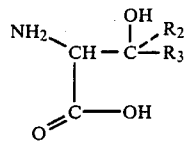

XV

The amino group is first protected (with a protecting group "$R_4$", e.g., t-butoxycarbonyl). The carboxyl group of the protected amino acid is then reacted with an amine having the formula

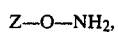

XVI wherein Z is alkyl, benzyl or triphenylmethyl, in the presence of a carbodiimide to yield a compound having the formula

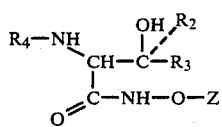

XVII

The hydroxyl group of a compound of formula XVII is converted to a leaving group ("OL) with a reagent, such as methanesulfonyl chloride or pyridine-$SO_3$ complex.

The fully protected compound having the formula

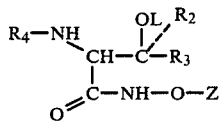

XVIII is cyclized by treatment with base, e.g., potassium carbonate. The reaction is preferably carried out in an organic solvent or an organic solvent/water mixture under reflux conditions, and yields a compound having the formula

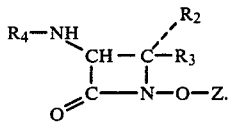

XIX

Alternatively, cyclization of a compound of formula XVII can be accomplished without first converting the hydroxyl group to a leaving group. Treatment of a compound of formula XVII with triphenylphosphine and diethylazodicarboxylate, yields a compound of formula XIX.

Exemplary procedures for the conversion of a compound of formula XVIII to a compound of formula XIX are described in *J. Amer. Chem. Soc.*, 102, 7026 (1980) and *J. Org. Chem.*, 47, 5160 (1982).

Both of the methods disclosed above for ring closure of a compound of formula XVII result in the inversion of the stereochemistry at the carbon atom bearing the $R_2$ and $R_3$ substituents when $R_2$ and $R_3$ are not the same.

Removal of the protecting group from the 1-position of an azetidinone of formula XIX can be accomplished via sodium reduction when Z is alkyl, and yields an intermediate having the formula $$\begin{array}{c} R_4-NH \\ \diagdown \\ CH-C \\ \diagup \quad \diagdown \\ O=C \quad R_3 \\ \diagdown \\ NH \end{array} \quad \text{II}$$

(at least one of $R_2$ and $R_3$ is hydrogen). If Z is benzyl, catalytic (e.g., palladium on charcoal) hydrogenation will initially yield the corresponding N-hydroxy compound, which upon treatment with titanium trichloride yields an intermediate of formula II. If Z is triphenylmethyl, formic acid or 70% acetic acid/water will initially yield the corresponding N-hydroxy compound. A $$\begin{array}{c} O \\ \parallel \\ -C-NH-SO_2-R \end{array}$$

activating group can be introduced in the 1-position of a compound of formula II using the procedures described above, and the resulting compound can be deprotected and acylated.

The nucleophiles of formula V wherein R is

[structure with $-A_1-N$, $N-A_2-C$, pyridone ring with OH]

and $A_1$ and $A_2$ are each a single bond can be prepared by reacting a silylated derivative of imidazolidin-2,4-dione $$(HN \quad NH),$$
with central C=O or the anion of imidazolidin-2,4-dione formed with a strong non-nucleophilic base, with an activated, suitably protected derivative of the acid having the formula

[structure XX: HO-pyridone-C(=O)-OH]

to obtain, upon deprotection, the corresponding compound having the formula

[structure XXI]

The reaction can be run in an inert organic solvent such as dimethylformamide, acetonitrile, dichloromethane, or tetrahydrofuran. The acid of formula XX can be activated with dicyclohexylcarbodiimide, or a combination of dicyclohexylcarbodiimide and hydroxybenzotriazole. An activated and suitably protected derivative of the compound of formula XX can also be the corresponding acid chloride (prepared with reagents such as phosphorus pentachloride, thionyl chloride, oxalyl chloride or triphenylphosphine/carbon tetrachloride) or a mixed anhydride (prepared with such reagents as diphenylphosphoryl chloride, pivaloyl chloride, or isobutyl chloroformate).

The compound of formula XX can be prepared as described in the literature; see *Helv. Chem. Acta*, 43, 469 (1960) and *J. Med. Chem.*, 17, 1 (1974).

The nucleophile of formula V wherein R is

[structure with $-A_1-N$, $N-A_2-C$, pyridone ring with OH]

$A_1$ is a single bond and $A_2$ is —NH— can be prepared by reacting an activated and optionally protected derivative of a compound of formula XX with 1-aminoimidazolidin-2,4-dione $$(HN \quad N-NH_2)$$

to yield upon deprotection

[structure XXII]

The nucleophiles of formula V wherein R is

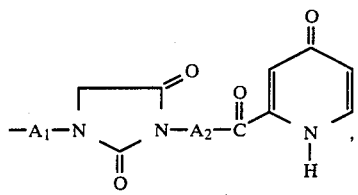

$A_1$ is a single bond and $A_2$ is —CH$_2$—CH$_2$—NH— can be prepared by reacting an activated and optionally protected derivative of a compound of formula XX with 1-(2-aminoethyl)imidazolidin-2,5-dione

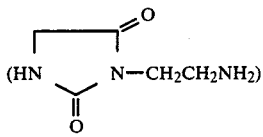

to yield upon deprotection

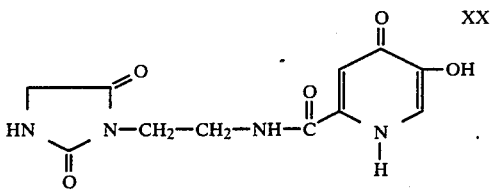   XXIII

The nucleophiles of formula V wherein R is

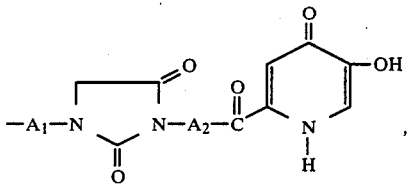

A is a single bond and A$_2$ is

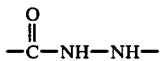

can be prepared by reacting

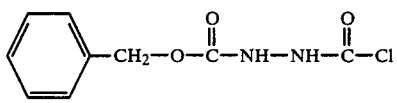   XXIV with a silylated form of imidazolidin-2,4-dione, the anion of imidazolidin-2,4-dione formed with a strong non-nucleophilic base, or with imidazolidin-2,4-dione in the presence of an organic base to yield

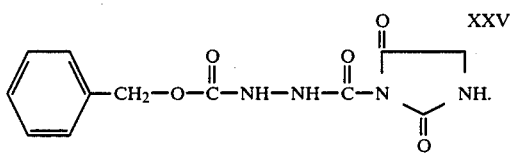   XXV

Catalytic hydrogenation of the compound of formula XXV yields the compound having the formula

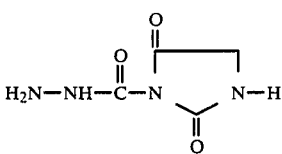   XXVI which can be coupled with an activated and optionally protected derivative of a compound of formula XX to yield, upon deprotection,

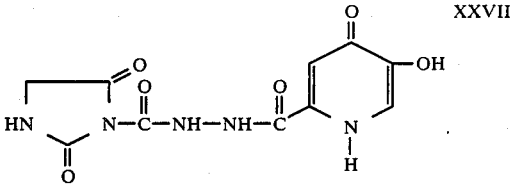   XXVII

Alternatively, the compound of formula XXVI can be prepared by first reacting 1-(chlorocarbonyl-)imidazolidin-2,5-dione with t-butoxycarbonyl protected hydrazine to yield

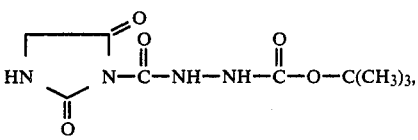   XXVIII and deprotecting the compound of formula XXVIII.

The nucleophiles of formula V wherein R is

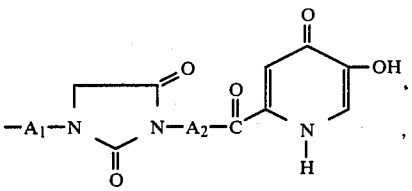

$A_1$ is

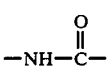

and A$_2$ is a single bond can be prepared by reacting a compound having the formula

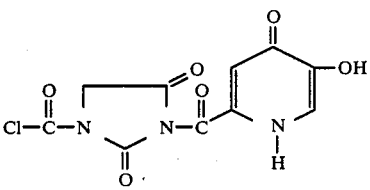   XXIX (suitably protected) with hexamethyldisilazane to yield upon hydrolysis and deprotection a compound having the formula

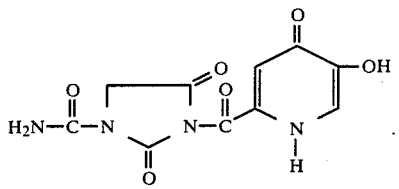
XXX

The compounds of formula XXIX (suitably protected) can be prepared by reacting a silylated form of a compound of formula XXI (optionally protected) with phosgene.

Alternatively, a compound of formula XXX can be prepared by reacting a protected form of a compound of formula XXI with chlorosulfonyl isocyanate followed by hydrolysis of the resulting intermediate and cleavage of the protecting groups.

The nucleophiles of formula V wherein R is

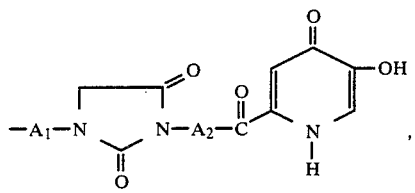

$A_1$ is

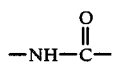

and $A_2$ is —NH— can be prepared by reacting a silylated form of the compound

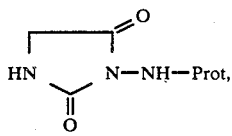
XXXI wherein the symbol Prot can be an amino protecting group such as t-butoxycarbonyl or benzyloxycarbonyl, with phosgene to yield

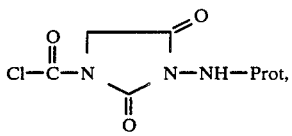
XXXII which can be reacted with hexamethylsilazane to yield upon deprotection

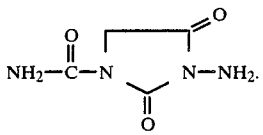
XXXIII

Reaction of the compound of formula XXXIII with an optionally protected activated form of a compound of formula XX yields upon deprotection

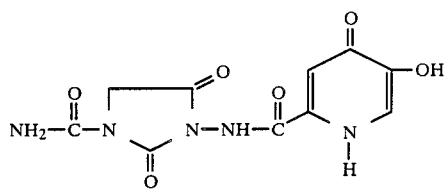
XXXIV

Alternatively, a compound of formula XXXIII can be prepared by reacting the compound having the formula

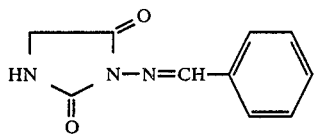
XXXV with chlorosulfonyl isocyanate to yield upon hydrolysis

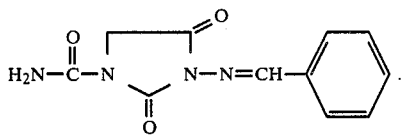
XXXVI

Treatment of this compound with aqueous acid yields a salt of the compound of formula XXXIII.

The nucleophiles of formula V wherein R is

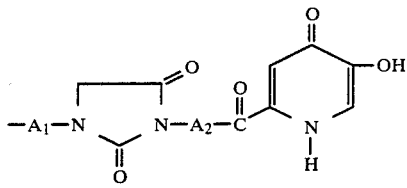

A is

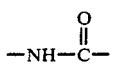

and $A_2$ is —CH$_2$—CH$_2$—NH— can be prepared by first deprotecting 1-(aminocarbonyl)-3-[2-[[(t-butoxy)carbonyl]amino]ethyl]imidazolidin-2,5-dione and coupling the resulting compound with an activated form of a compound of formula XX (optionally protected) to obtain after deprotection

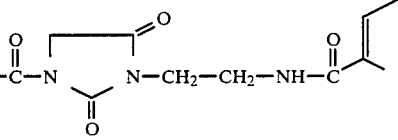
XXXVII

The nucleophiles of formula V wherein R is

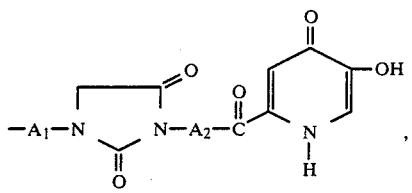

A₁ is

and A₂ is

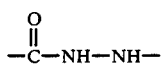

can be prepared by reacting a silylated form of a compound of formula XXVII (optionally protected) with phosgene followed by hexamethyldisilazane to yield upon hydrolysis and deprotection

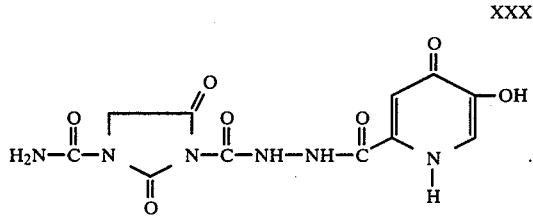

XXXVIII

Alternatively, a compound of formula XXXVIII can be prepared by reacting a protected form of a compound of formula XXVII with chlorosulfonylisocyanate followed by hydrolysis of the resulting intermediate and cleavage of the protecting groups. Alternatively, compound XXV can be reacted with chlorosulfonyl isocyanate followed by hydrolysis of the resulting intermediate to yield

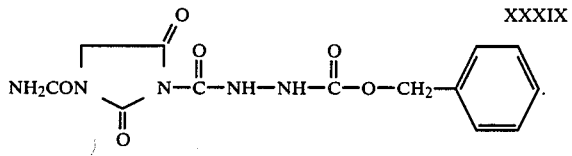

XXXIX

Deprotection of XXXIX by hydrogenolysis yields

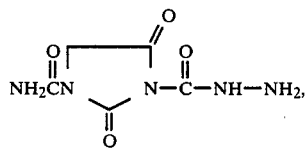

XL which can be coupled with an activated and optionally protected derivative of a compound of formula XX to yield upon deprotection a compound of formula XXXVIII.

The nucleophiles of formula V wherein R is

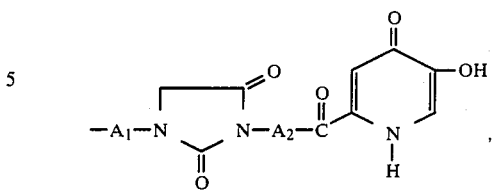

A₁ is —NH— and A₂ is a single bond can be prepared by coupling a compound having the formula

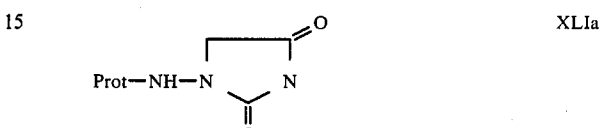

XLIa with an activated form of a compound of formula XX (optionally protected) and cleaving the protecting group to yield

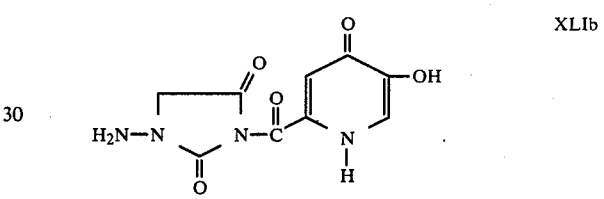

XLIb

The nucleophiles of formula V wherein R is

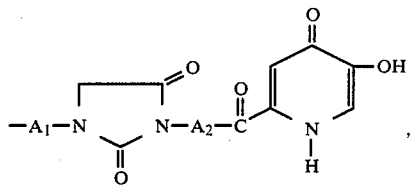

A₁ is —NH— and A₂ is —NH— can be prepared by coupling a monoprotected (preferably with t-butoxycarbonyl or benzyloxycarbonyl) derivative of 1,3-(diamino)imidazolidin-2,5-dione with an activated form of a compound of formula XX (optionally protected) and deprotecting the resulting compound to yield

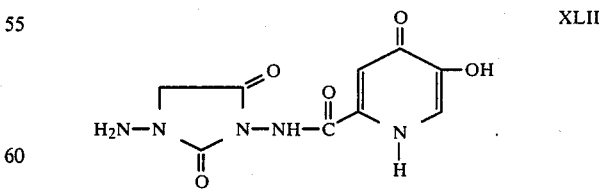

XLII

Alternatively, a compound of formula XLII can be formed by nitrosating a protected form of a compound of formula XXII followed by reduction of the nitroso group and cleavage of the protecting groups.

The nucleophiles of formula V wherein R is

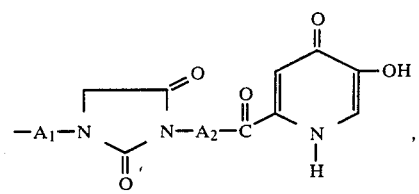

$A_1$ is —NH— and $A_2$ is —CH$_2$—CH$_2$—NH— can be prepared by nitrosating a compound of formula XXIII (suitably protected) to yield a compound having the formula

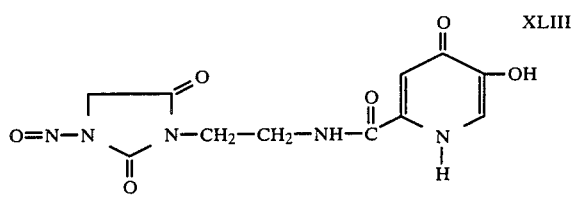

XLIII (suitably protected) and reducing and deprotecting that compound to yield

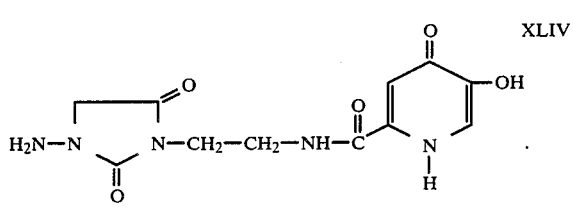

XLIV

The nucleophiles of formula V wherein R is

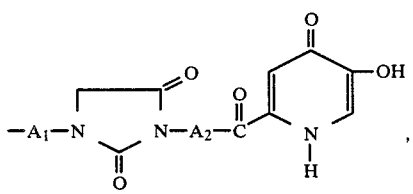

$A_1$ is —NH— and $A_2$ is

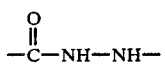

can be prepared by nitrosating, reducing and deprotecting a protected derivative of a compound of formula XXVII. The resulting compound has the formula

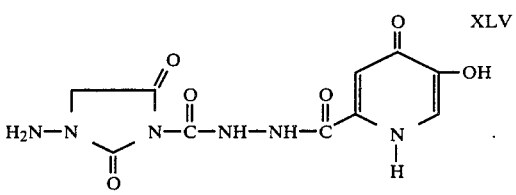

XLV

Alternatively, a compound of formula XLV can be prepared by reacting a compound of formula XXXI with phosgene to yield

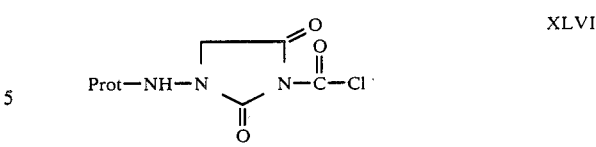

XLVI which, on reaction with a monoprotected hydrazine in the presence of base, yields

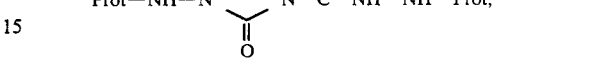

XLVII (The two protecting groups must be different). Selective removal of the hydrazide protecting group yields

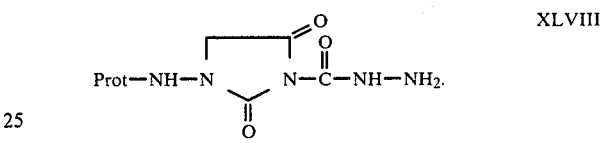

XLVIII

Coupling of a compound of formula XLVIII with an activated optionally protected form of a compound of formula XX, followed by deprotection, yields a compound of formula XLV.

The nucleophiles of formula V wherein R is

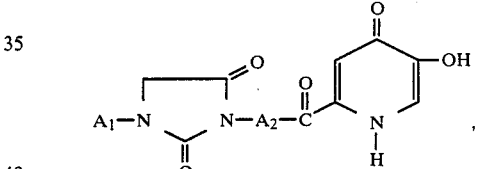

$A_1$ is

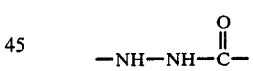

and $A_2$ is a single bond can be prepared by reacting a compound of formula XXIX (preferably a protected derivative thereof) with hydrazine (preferably in monoprotected form) in the presence of a base or with a silylated form of hydrazine or monoprotected hydrazine to yield a protected derivative of

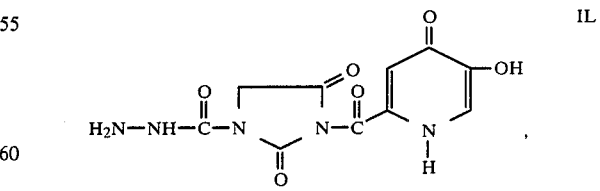

IL which can be deprotected using conventional techniques.

Alternatively, a compound of formula XXVIII (either a silylated derivative thereof or an anion thereof formed by reaction with a strong base) can be reacted with an activated form of formula XX (suitably protected) and deprotected to yield a compound of formula IL.

The nucleophiles of formula V wherein R is

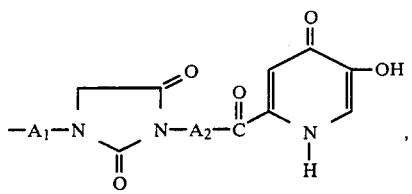

A₁ is

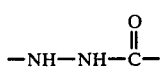

and A₂ is —NH— can be prepared by selective removal of the non-hydrazide protecting group of a compound of formula XLVII, followed by coupling with an activated optionally protected compound of formula XX and subsequent deprotection to yield a compound having the formula

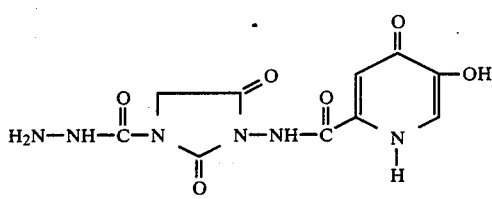
L

The nucleophiles of formula V wherein R is

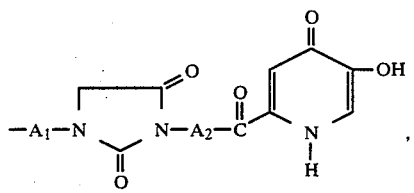

A₁ is

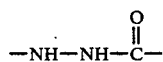

and and A₂ is —CH₂—CH₂—NH— can be prepared by sequentially reacting a compound of formula XXIII (or a protected derivative thereof) with phosgene followed by hydrazine (or a monoprotected derivative thereof) in the presence of a silylating agent such as N-methyl-N-(trimethylsilyl)trifluoroacetamide to yield upon deprotection

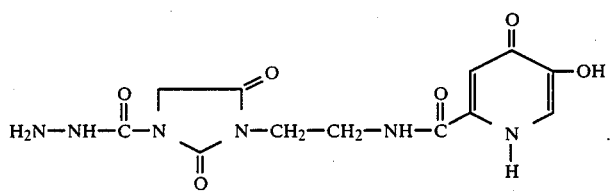

Alternatively, an amino protected derivative of 1-(2-aminoethyl)imidazolidin-2,5-dione (optionally silylated) can be reacted with phosgene, and then with a monoprotected derivative of hydrazine in the presence of a base or a silylating agent (e.g., N-methyl-N-(trimethylsilyl)trifluoroacetamide or bis(trimethylsilyl)acetamide) to yield a protected derivative of the compound having the formula

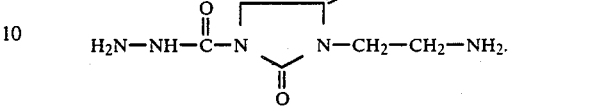
LII

The groups used to protect the terminal amino groups in a compound of formula LII should have been chosen so that the protecting group on the aminoethyl group can be selectively removed. The resulting mono-deprotected compound can be coupled with an activated form of an acid of formula XX (or a protected derivative thereof) to yield (after deprotection) a compound of formula LI.

The nucleophiles of formula V wherein R is

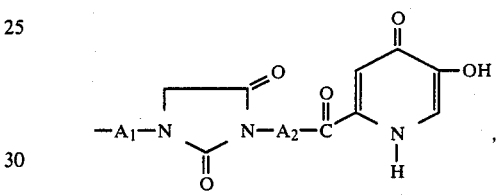

A₁ is

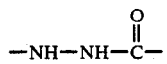

and A₂ is

can be prepared by reacting the compound of formula XXV (optionally as a silylated derivative thereof) with phosgene to yield a protected derivative of the compound having the formula

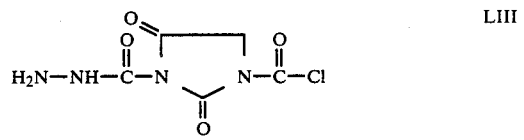
LIII which can be coupled with a protected derivative of hydrazine to yield a protected derivative of

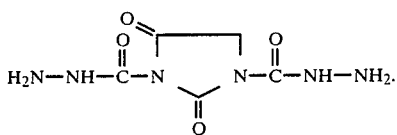

LIV

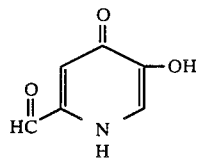

LVII

The groups used to protect the terminal amino groups in a compound of formula LIV should be chosen so that one of the protecting groups can be selectively removed. The resulting mono-deprotected compound can be coupled with an optionally protected activated form of an acid of formula XX to yield (after deprotection) a compound having the formula to yield, after removal of the $R_4$ protecting group and subsequent acylation, the corresponding compound having the formula

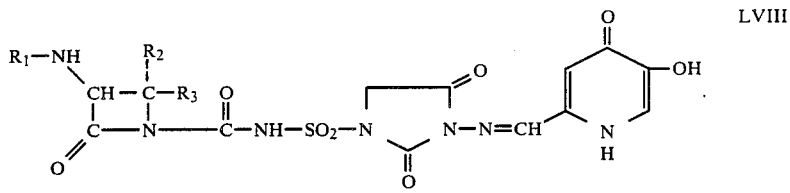

LVIII

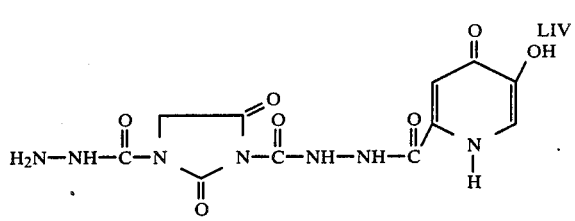

LIV

An alternative synthesis for the preparation of the compounds of this invention wherein R is A compound of formula LVI can be reacted with a suitably protected derivative of the acid of formula XX to yield, after deprotection and acylation, the corresponding compound of formula I wherein R is

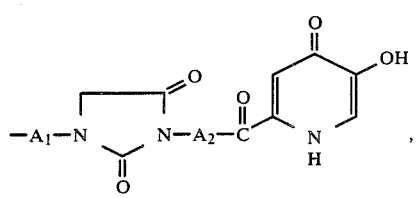

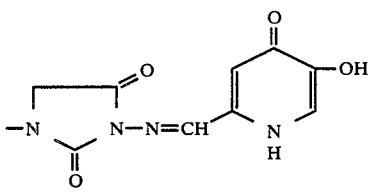

$A_1$ is a single bond and $A_2$ is —NH—.

A compound of formula I wherein R is

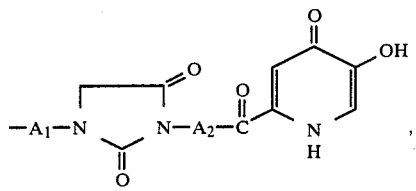

comprises first reacting a compound of formula IV with a compound having the formula

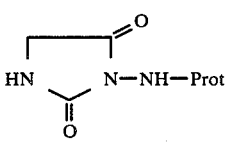

LV $A_1$ is —NH— and $A_2$ is a single bond can also be prepared by reacting a compound of formula IV with 1-aminoimidazolidin-2,4-dione. The resulting product can be reacted with a suitably protected derivative of the acid of formula XX to yield, after deprotection and acylation, the desired compound of formula I.

to yield, upon deprotection, the corresponding compound having the formula

The compounds described herein are pictured with the organic group

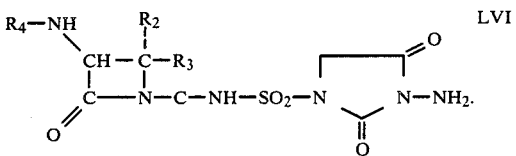

LVI

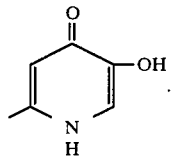

A compound of formula LVI can be reacted with a compound having the formula

This group exists in a tautomeric equilibrium with a group of the formula

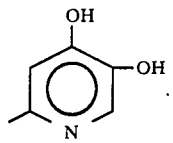

Depending on the additional substituent to the group, one form or the other will predominate. Both forms are meant to be included herein.

The following example is a specific embodiment of this invention.

EXAMPLE 1

[3S(Z)]-2-[[[1-(2-Amino-thiazolyl)-2-[[1-[[[[3-[[(1,4-dihydro-5-hydroxy-4-oxo-2-pyridinyl)carbonyl]amino]-2,4-dioxo-1-imidazolidinyl]sulfonyl]amino]carbonyl]-2-oxo-3-azetidinyl]amino]-2-oxoethylidene]amino]oxy]-2-methylpropanoic acid (A)

N-(2,5-Dioxo-1-imidazolidinyl)-1,4-dihydro-4-oxo-5-(phenylmethoxy)-1-(phenylmethyl)-2-pyridinecarboxamide 11.51 Grams (0.1 mol) of 1-amino-2,5-dioxo-imidazolidine were suspended in 200 ml of acetonitrile. After the addition of 55.65 ml of N-methyl-N-(trimethylsilyl)trifluoroacetamide (0.3 mol), the mixture was stirred at 50° C. to form a clear solution. After stirring the solution for 1 hour at room temperature, it was cooled with ice water and 1,4-dihydro-4-oxo-5-(phenylmethoxy)-1-(phenylmethyl)-2-pyridinecarbonyl chloride, prepared from 0.1 mol of the corresponding acid, was added all at once. The mixture was stirred overnight at room temperature and 20 ml of methanol were added together with a few drops of acetic acid. A precipitate formed. Stirring was continued for 2 hours and the precipitate was removed by filtration. It mainly consisted of starting material. The filtrate was evaporated in vacuo and the residue treated with water. It solidified and was filtered off to yield 40 g of crude N-(2,5-dioxo-1-imidazolidinyl)-1,4-dihydro-4-oxo-4-(phenylmethoxy)-1-(phenylmethyl)-2-pyridinecarboxamide. The crude material was refluxed with 500 ml of ethanol, cooled, filtered off and dried to yield 20.6 g of purified product.

(B)

N-(2,5-Dioxo-1-imidazolidinyl)-1,4-dihydro-4-oxo-5-hydroxy-2-pyridinecarboxamide To a solution of 10.8 g (0.025 mol) of N-(2,5-dioxo-1-imidazolidinyl)-1,4-dihydro-4-oxo-5-(phenylmethoxy)-1-(phenylmethyl)-2-pyridinecarboxamide in 200 ml of dimethylformamide was added 3.83 ml of trifluoroacetic acid (0.05 mol) and 6 g of palladium on charcoal (10%). With vigorous stirring, hydrogen was passed through the solution for 45 minutes. The catalyst was removed by filtration and the filtrate evaporated. The remaining syrup solidified on trituration with ether. Yield: 6.1 g, melting point 260°–270° C., dec.

(C)

(S)-[1-[[[[3-[[(1,4-Dihydro-5-hydroxy-4-oxo-2-pyridinyl)carbonyl]amino]-2,4-dioxo-1-imidazolidinyl]-]sulfonyl]amino]carbonyl]-2-oxo-3-azetidinyl]carbamic acid, phenylmethyl ester, sodium salt To a suspension of 6.1 g (0.0242 mol) of N-(2,5-dioxo-1-imidazolidinyl)-1,4-dihydro-4-oxo-5-hydroxy-2-pyridinecarboxamide in 200 ml of ethyl acetate was added 19.48 ml of N-methyl-N-(trimethylsilyl)trifluoroacetamide (0.105 mol) at room temperature. The mixture was stirred at room temperature for 1 hour. After stirring for 10 minutes, a clear solution was formed (solution A).

To a suspension of 5.32 g of (S)-(2-oxo-3-azetidinyl)-carbamic acid, phenylmethyl ester (0.242 mol) in 200 ml of ethyl acetate was added at room temperature with stirring 2.11 ml (0.0242 mol) of chlorosulfonylisocyanate. The mixture was stirred at room temperature for 1 hour. After 10 minutes, a clear solution was formed (solution B).

Solution A was added, with cooling, to solution B and the mixture was stirred overnight at room temperature. Then the solution was evaporated in vacuo and the remaining syrup dissolved in a mixture of 150 ml of acetone and 150 ml of water. The pH of the clear solution was adjusted to 5–5.5 by the addition of a sodium bicarbonate solution. The solution as kept at this pH for 2 hours. Then the acetone was removed in vacuo, and the aqueous solution lyophilized to yield 14.6 g of crude of (S)-[1-[[[[3-[[(1,4-dihydro-5-hydroxy-4-oxo-2-pyridinyl)carbonyl]amino]-2,4-dioxo-1-imidazolidinyl]-sulfonyl]amino]carbonyl]-2-oxo-3-azetidinyl]carbamic acid, phenylmethyl ester, sodium salt. The crude material was purified by chromatography on XAD by elution with water/acetone (9:1). Yield: 2.5 g of purified product.

(D)

(S)-N-[3-[[[[(3-Amino-2-oxo-1-azetidinyl)carbonyl]amino]sulfonyl]-2,4-dioxo-1-imidazolidinyl]-1,4-dihydro-5-hydroxy-4-oxo-2-pyridinecarboxamide, trifluoroacetate salt 2.5 Grams (0.0042 mol) of (S)-[1-[[[[3-[[(1,4-dihydro-5-hydroxy-4-oxo-2-pyridinyl)carbonyl]amino]-2,4-dioxo-1-imidazolidinyl]sulfonyl]amino]carbonyl]-2-oxo-3-azetidinyl]carbamic acid, phenylmethyl ester, sodium salt were added at 10° C. to a mixture of 10 ml of trifluoroacetic acid and 2 ml of thioanisole and stirred overnight at 10° C. The mixture was evaporated in vacuo and (S)-N-[3-[[[(3-amino-2-oxo-1-azetidinyl)carbonyl]amino]sulfonyl]-2,4-dioxo-1-imidazolidinyl]-1,4-dihydro-5-hydroxy-4-oxo-2-pyridinecarboxamide, trifluoroacetate salt was precipitated by the addition of 20 ml of ethyl acetate followed by 30 ml of ether. Yield: 2.7 g of crude product.

(E)

[3S(Z)]-2-[[[1-(2-Amino-4-thiazolyl)-2-[[1-[[[[3-[[(1,4--dihydro-5-hydroxy-4-oxo-2-pyridinyl)carbonyl]amino]-2,4-dioxo-1-imidazolidinyl]sulfonyl]amino]carbony]-2-oxo-3-acetidinyl]amino]-2-oxoethylidene]amino]oxy]-2-methylpropanoic acid, diphenylmethyl ester To a suspension of 1.76 g (0.004 mol) of (Z)-2-amino-α-[(1-diphenylmethoxycarbonyl-1-methylethoxy)imino]-4-thiazoleacetic acid in 30 ml of acetonitrile was added, at −30° C., 1.67 ml of triethylamine (0.012 mol) followed by 0.88 ml of diphenylchlorophosphate. The mixture was stirred at −30° C. for 1½ hours (reaction mixture A).

To a suspension of 2.7 g (0.004 mol) of (S)-N-[3-[[[(3-amino-2-oxo-1-azetidinyl)carbonyl]amino]sulfonyl]-2,4-dioxo-1-imidazolidinyl]-1,4-dihydro-5-hydroxy-4-oxo-2-pyridinecarboxamide, trifluoroacetate salt in 30 ml of ethyl acetate were added, at room temperature, 2.96 ml of bistrimethylsilylacetamide (0.012 mol). After stirring for 20 minutes, a clear solution was formed, the solution was cooled to 0° C. and added within five minutes to the reaction mixture A. The temperature was kept between −30° C. and −25° C. Then the reaction mixture was stirred at −10° C. for 1½ hours and at 0° C. for 1 hour. After evaporation of the solvent in vacuo, the remaining syrup was treated with water to yield 3.1 g of crude product.

(F)
[3S(Z)]-2-[[[1-(2-Amino-4-thiazolyl)-2-[[1-[[[[3-[[1,4-d-ihydro-5-hydroxy-4-oxo-2-pyridinyl)carbonyl]amino]-2,4-dioxo-1-imidazolidinyl]sulfonyl]amino]carbonyl]-2-oxo-3-azetidinyl]amino]-2-oxoethylidene]amino]oxy]-2-methylpropanoic acid 3.1 Grams of crude [3S(Z)]-2-[[[1-(2-amino-4-thiazolyl)-2-[[1-[[[[3-[[(1,4-dihydro-5-hydroxy-4-oxo-2--pyridinyl)carbonyl]amino]-2,4-dioxo-imidazolidinyl]-sulfonyl]amino]carbonyl]-2-oxo-3-azetidinyl]amino]-2-oxoethylidene]amino]oxy]-2-methylpropanoic acid, diphenylmethyl ester was added at −10° C. to a mixture of 31 ml of trifluoroacetic acid and 6.2 ml of anisole. After stirring for 1 hour at −10° C., the crude trifluoroacetic acid salt of [3S(Z)]-2-[[[1-(2-amino-4-thiazolyl)-2-[[1-[[[3-[[(1,4-dihydro-5-hydroxy-4-oxo-2-pyridinyl)-carbonyl]amino]-2,4-dioxo-1-imidazolidinyl]sulfonyl]amino]carbonyl]-2-oxo-3-azetidinyl]amino]-2-oxoethylidene]amino]oxy]-2-methylpropanoic acid was precipitated by the addition of ether (2.7 g).

The crude product was dissolved in a mixture of 10 ml of water and 10 ml of acetone, and the pH was adjusted to 5.5–6 by the addition of 2N sodium hydroxide. After evaporation of the acetone and lyophilization of the water, 2.7 g of crude sodium salt of [3S(Z)]-2-[[[1--(2-amino-4-thiazolyl)-2-[[1-[[[[3-[[(1,4-dihydro-5-hydroxy-4-oxo-2-pyridinyl)carbonyl]amino]-2,4-dioxo-1-imidazolidinyl]sulfonyl]amino]carbonyl]-2-oxo-3-azetidinyl]amino]-2-oxoethylidene]amino]oxy]-2-methylpropanoic acid was obtained. The crude product was purified by chromatography on XAD-2. The sodium salt of [3S(Z)]-2-[[[1-(2-amino-4-thiazolyl)-2-[[1-[[[[3-[[(1,4-dihydro-5-hydroxy-4-oxo-2-pyridinyl)carbonyl]amino]-2,4-dioxo-1-imidazolidinyl]sulfonyl]amino]carbonyl-2-oxo-3-azetidinyl]amino]-2-oxoethylidene]amino]oxy]-2-methylpropanoic acid was eluted with water to yield 0.6 g of purified material. For further purification, the sodium salt was dissolved in a mixture of 10 ml of water and 5 ml of acetone and the pH of the mixture was adjusted to 1.5. The free acid thus obtained was again purified by column chromatography on XAD-2. [3S(Z)]-2-[[[1-(2-Amino-4-thiazolyl)-2-[[1-[[[[3-[[(1,4-dihydro-5-hydroxy-4-oxo--2-pyridinyl)carbonyl]amino]-2,4-dioxo-1-imidazolidinyl]sulfonyl]amino]carbonyl-2-oxo-3-azetidinyl]amino]-2-oxoethylidene]amino]oxy]-2-methylpropanoic acid was eluted with acetone/water (5:95). Yield: 0.1 g of product.

What is claimed is:
1. A compound having the formula

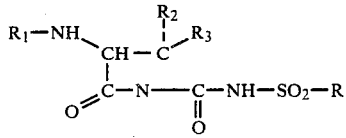

or a pharmaceutically acceptable salt thereof wherein

R is 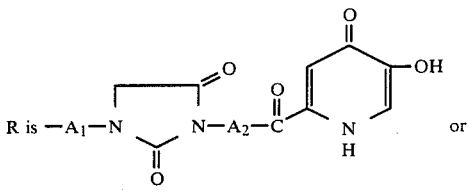 or

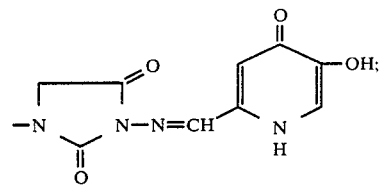

$R_1$ is an acyl group derived from a carboxylic acid;
$R_2$ and $R_3$ are the same or different and each is hydrogen, alkyl, alkenyl, alkynyl, cycloalkyl, phenyl, substituted phenyl or a 4, 5, 6 or 7-membered heterocycle or one of $R_2$ and $R_3$ is hydrogen and the other is azido, halomethyl, dihalomethyl, trihalomethyl, alkoxycarbonyl, 2-phenylethenyl, 2-phenylethynyl, carboxyl,

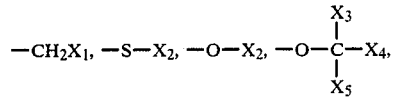

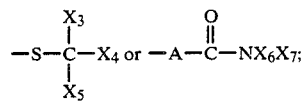

$X_1$ is azido, amino, hydroxy, carboxyl, alkoxycarbonyl, alkanoylamino, phenylcarbonylamino, (substituted phenyl)carbonylamino, alkylsulfonyloxy, phenylsulfonyloxy, (substituted phenyl)sulfonyloxy, phenyl, substituted phenyl, cyano,

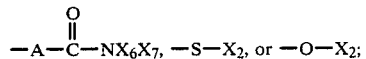

$X_2$ is alkyl, substituted alkyl, phenyl, substituted phenyl, phenylalkyl, (substituted phenyl)alkyl, alkanoyl, phenylakanoyl, (substituted phenyl)alkanoyl, phenylcarbonyl, (substituted phenyl)carbonyl, or heteroarylcarbonyl;

one of $X_3$ and $X_4$ is hydrogen and the other is hydrogen or alkyl, or $X_3$ and $X_4$ when taken together with the carbon atom to which they are attached form a cycloalkyl group;

$X_5$ is formyl, alkanoyl, phenylcarbonyl, (substituted phenyl)carbonyl, phenylalkylcarbonyl, (substituted phenyl)alkylcarbonyl, carboxyl, alkoxycarbonyl, aminocarbonyl, (substituted amino)carbonyl, or cyano;

$X_6$ and $X_7$ are the same or different and each is hydrogen, alkyl, phenyl or substituted phenyl, or $X_6$ is hydrogen and $X_7$ is amino, substituted amino, alkanoylamino or alkoxy, or $X_6$ and $X_7$ when taken together with the nitrogen atom to which they are attached form a 4, 5, 6 or 7-membered heterocycle;

A is —CH=CH—, —(CH$_2$)$_m$—, —(CH$_2$)$_m$—O—, —(CH$_2$)$_m$—NH— or —CH$_2$—S—CH$_2$—;

m is 0, 1 or 2;

A$_1$ is a single bond,

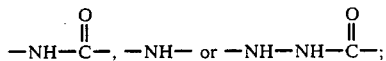

and

A$_2$ is a single bond,

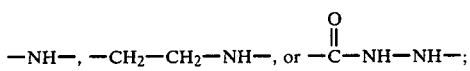

the term "substituted phenyl" refers to a phenyl group substituted with 1, 2, or 3 amino, halogen, hydroxyl, trifluoromethyl, alkyl of 1 to 4 carbon atoms, alkoxy of 1 to 4 carbon atoms, alkanoyloxy, aminocarbonyl, or carboxy groups;

the term "substituted alkyl" refers to alkyl groups substituted with one or more azido, amino, halogen, hydroxy, carboxy, cyano, alkoxycarbonyl, aminocarbonyl, alkanoyloxy, alkoxy, phenyloxy, (substituted phenyl)oxy, mercapto, alkylthio, phenylthio, (substituted phenyl)thio, alkylsulfinyl or alkylsulfonyl groups;

the term "heteroaryl" refers to pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, tetrazolyl or one of the above groups substituted with one or more halogen, hydroxy, nitro, amino, cyano, trifluoromethyl, alkyl of 1 to 4 carbon atoms, alkoxy of 1 to 4 carbon atoms, alkylsulfonyl, phenyl, substituted phenyl, 2-furfurylideneamino, benzylideneamino or substituted alkyl, wherein the alkyl group has 1 to 4 carbon atoms, groups;

the term "a 5, 6 or 7-membered heterocycle" refers to pyridinyl, furanyl pyrrolyl, thienyl, 1,2,3-triazolyl, 1,2,4-triazolyl, imidazolyl, thiazolyl, thiadiazolyl, pyrimidinyl, oxazolyl, triazinyl, tetrazolyl, azetidinyl, oxetanyl, thietanyl, piperidinyl, piperazinyl, imidazolidinyl, oxazolidinyl, pyrrolidinyl, tetrahydropyrimidinyl, dihydrothiazolyl or hexahydroazepinyl or one of the above groups substituted with one or more oxo, halogen, hydroxy, nitro, amino, cyano, trifluoromethyl, alkyl of 1 to 4 carbon atoms, alkoxy of 1 to 4 carbon atoms, alkylsulfonyl, phenyl, substituted phenyl, 2-furfurylideneamino, benzylideneamino or substituted alkyl, wherein the alkyl group has 1 to 4 carbon atoms, groups;

the term "substituted amino" refers to a group having the formula —NX$_8$X$_9$ wherein X$_8$ is hydrogen, alkyl, phenyl, substituted phenyl, phenylalkyl or (substituted phenyl)alkyl, and X$_9$ is alkyl, phenyl, substituted phenyl, phenylalkyl, (substituted phenyl)alkyl, hydroxy, cyano, alkoxy, phenylalkoxy or amino.

2. A compound in accordance with claim 1 wherein R is

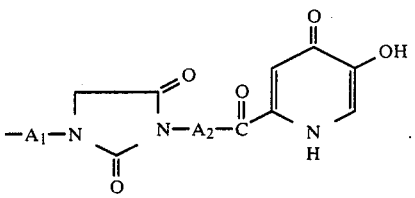

3. A compound in accordance with claim 1 wherein R is

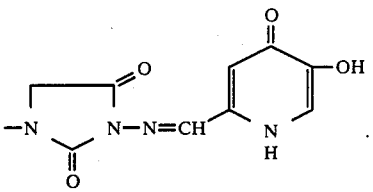

4. A compound in accordance with claim 2 wherein A$_1$ is a single bond.

5. A compound in accordance with claim 2 wherein A$_1$ is

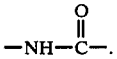

6. A compound in accordance with claim 2 wherein A$_1$ is —NH—.

7. A compound in accordance with claim 2 wherein A$_1$ is

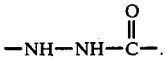

8. A compound in accordance with claim 2 wherein A$_2$ is a single bond.

9. A compound in accordance with claim 2 wherein A$_2$ is —NH—.

10. A compound in accordance with claim 2 wherein A$_2$ is —CH$_2$—CH$_2$—NH—.

11. A compound in accordance with claim 2 wherein A$_2$ is

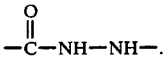

12. A compound in accordance with claim 2 wherein A$_1$ is a single bond and A$_2$ is —NH—.

13. A compound in accordance with claim 1 wherein R$_2$ and R$_3$ are each hydrogen.

14. A compound in accordance with claim 1 wherein R$_1$ is

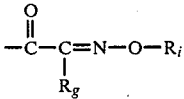

and R$_g$ is 2-amino-4-thiazolyl and R$_i$ is methyl, ethyl, carboxymethyl, 1-carboxy-1-methylethyl, 1-carboxyl-1-ethyl, or

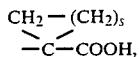

wherein s is 1, 2 or 3.

15. A compound in accordance with claim 1 wherein $R_1$ is

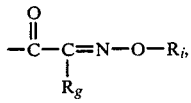

$R_g$ is 2-amino-4-thiazolyl and $R_i$ is carboxymethyl, 1-carboxy-1-methylethyl, 1-carboxy-1-ethyl, or

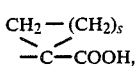

wherein s is 1, 2 or 3.

16. A compound in accordance with claim 12 wherein $R_1$ is

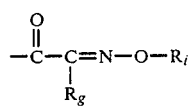

and $R_g$ is 2-amino-4-thiazolyl and $R_i$ is methyl, ethyl, carboxymethyl, 1-carboxy-1-methylethyl, 1-carboxy-1-ethyl or

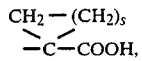

wherein s is 1, 2 or 3.

17. A compound in accordance with claim 12 wherein $R_1$ is

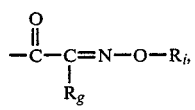

$R_g$ is 2-amino-4-thiazolyl and $R_i$ is carboxymethyl or 1-carboxy-1-methylethyl.

18. A compound in accordance with claim 12 wherein $R_2$ and $R_3$ are each hydrogen.

19. The compound in accordance with claim 1, [3-S(Z)]-2-[[[1-(2-amino-thiazolyl)-2-[[1-[[[3-[[(1,4-dihydro-5-hydroxy-4-oxo-2-pyridinyl)carbonyl]amino]-2,4-dioxo-1-imidazolidinyl]sulfonyl]amino]carbonyl]-2-oxo-3-azetidinyl]amino]-2-oxoethylidene]amino]oxy]-2-methylpropanoic acid, or a pharmaceutically acceptable salt thereof.

* * * * *